(12) United States Patent
Cull

(10) Patent No.: US 6,554,847 B2
(45) Date of Patent: Apr. 29, 2003

(54) ZERO COMPRESSION MICROKERATOME CUTTING HEAD ASSEMBLY

(75) Inventor: Laurence J. Cull, Wildwood, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 47 days.

(21) Appl. No.: 09/738,129

(22) Filed: Dec. 15, 2000

(65) Prior Publication Data

US 2002/0077639 A1 Jun. 20, 2002

(51) Int. Cl.$^7$ .................................................. A61F 9/00
(52) U.S. Cl. ....................................................... 606/166
(58) Field of Search .............................. 606/4, 5, 161, 606/162, 166, 167, 169, 170, 171, 172, 173, 180

(56) References Cited

U.S. PATENT DOCUMENTS 5,591,174 A * 1/1997 Clark et al. .................. 606/130
5,624,456 A * 4/1997 Hellenkamp ................ 606/166

* cited by examiner

Primary Examiner—John J. Calvert
Assistant Examiner—Shaun R Hurley
(74) Attorney, Agent, or Firm—Michael L. Smith

(57) ABSTRACT

A microkeratome cutting head assembly 10. A cutting blade 14 of the assembly 10 has a nominal length and presents a forward cutting edge 22. An applanation member 12 for applanating a cornea of an eye includes a trailing portion 18 having a curved section presenting an apex 20. The forward cutting edge 22 of the cutting blade 14 of the nominal length is positioned relative to the apex 20 so that together the forward cutting edge 22 and the apex 20 define a desired thickness of a flap 50 to be created from the cornea 48 such that the flap 50 is essentially not compressed.

6 Claims, 1 Drawing Sheet

ZERO COMPRESSION MICROKERATOME CUTTING HEAD ASSEMBLY

BACKGROUND OF THE INVENTION

I. Field of the Invention

The present invention relates to the field of ophthalmic microkeratomes and, more particularly, to microkeratome cutting head assemblies for cutting a corneal flap to prepare a patient's eye for refractive surgery.

II. Description of the Related Art

The use of microkeratomes in creating a corneal flap for preparing an eye for refractive surgery such as laser-assisted instuikeratomileusis (LASIK) are well known. Typically, a microkeratome cuts a flap of corneal tissue by movement of a blade (either oscillating or non-oscillating) across a cornea of a patient's eye. The movement of the blade against the cornea typically stops before the corneal flap becomes detached from the cornea. Such microkeratomes are well known and their movement may be arcuate, as described in U.S. Pat. No. 5,624,456, titled Automatic Surgical Device For Cutting a Cornea, by Johann Hellenkamp which is incorporated herein by reference. However, a microkeratome may also translate a blade across the cornea in a linear straight-line fashion which is well-known in the art.

It is common for known microkeratomes to applanate, or flatten-out, the cornea of patient's eye before the cutting blade of the microkeratome begins to create the flap. This applanation causes the cornea to form a flat surface so that the flat blade may create a proper thickness of cut in the cornea and provide a surgeon with a properly sized flap thickness and diameter.

What has not been appreciated until now is the relationship between a cutting blade's forward cutting edge and the trailing portion of an applanation member of a microkeratome cutting head assembly. When forming a corneal flap, it is important to prevent damage to the greatest extent possible to the thin epithelial layer of the cornea. Any damage to the epithelial layer of the cornea can cause discomfort and temporarily diminish sight of a patient. In this regard, it is believed that if the forward cutting edge is not positioned properly with respect to the trailing portion of the applanation member, compression of the corneal flap can occur resulting in damage to the epithelial layer of the created corneal flap.

Therefore, there is a need to ensure that compression of the created corneal flap is reduced to minimize potential epithelial damage to the corneal flap.

DETAILED DESCRIPTION OF THE PREFERRED EMBODIMENT

Figure 1:
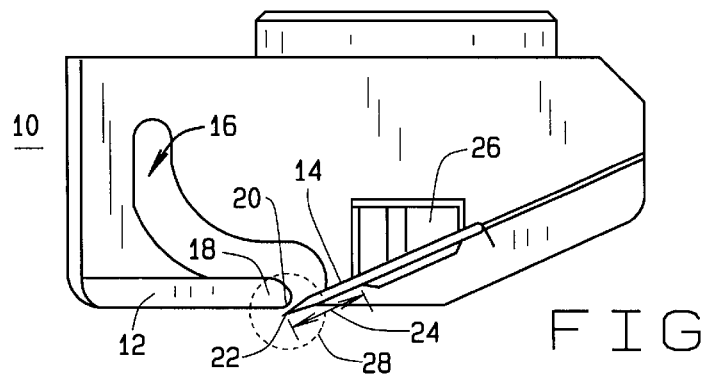
FIG. 1 is an elevational view of a microkeratome cutting head assembly, in accordance with the present invention.

Microkeratome cutting head assembly 10 is shown in FIG. 1 and includes an applanation member 12, a cutting blade 14, and a recessed area 16 for accepting a corneal flap cut by assembly 10. Applanation member 12 includes trailing portion 18 having a curved section presenting apex 20. Cutting blade 14 has a forward cutting edge 22 and a nominal length 24, in addition to a blade holder 26 for securing the blade within cutting head assembly 10.

Figure 2:
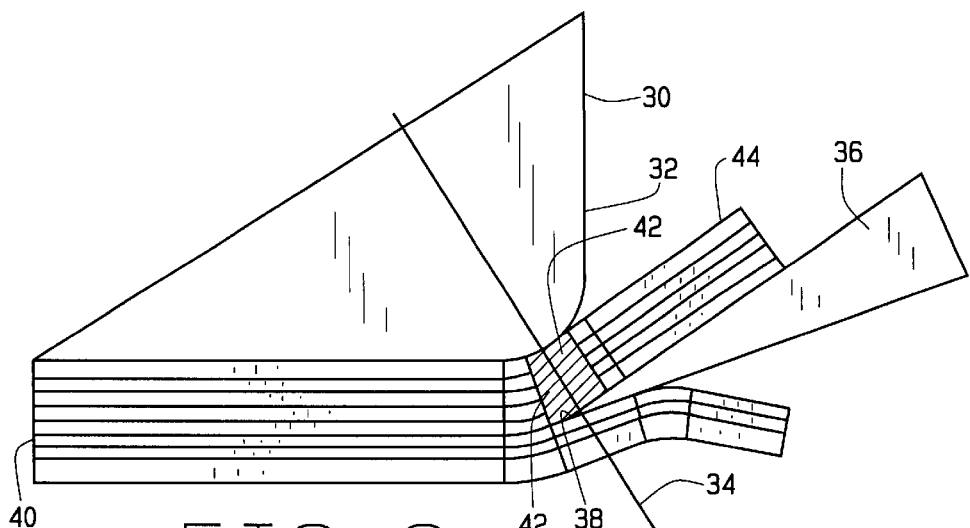
FIG. 2 is a partial view of a prior art microkeratome cutting head assembly.
Figure 3:
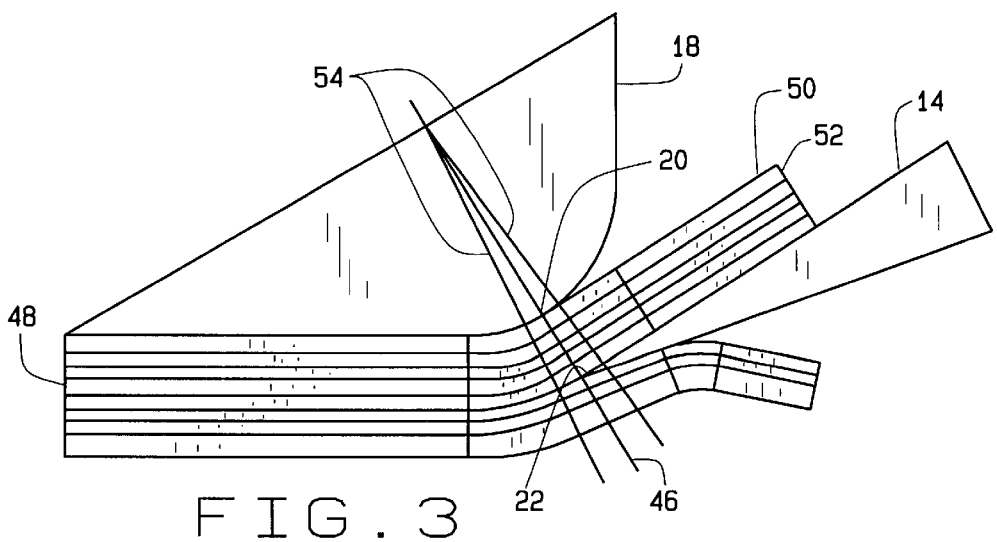
FIG. 3 is a partial view of a microkeratome cutting head assembly, in accordance with the present invention.

Dashed circle 28 generally defines the area which is illustrated in FIGS. 2 and 3 below and is a particular concern to the present invention.

In use, cutting head assembly 10 moves across a cornea of a patient's eye where cutting edge 22 contacts the cornea and begins to form a corneal flap which is held within recess 16 as assembly 10 moves across the patient's cornea. The formed corneal flap is preferably between 120 micron and 200 microns thick, depending on a patient's corneal topography, the required refractive correction, and the particular assembly 10 chosen.

FIG. 2 shows a prior art microkeratome cutting head assembly having a trailing portion 30 with an apex 32 defined by line 34 that is positioned relative to cutting blade 36 where a forward cutting edge 38 of blade 36 extends beyond line 34. This results in compression of cornea 40 as shown in shaded areas 42. In testing, using a computer model simulation, the compression of the corneal flap 44 has been calculated to be approximately 10.9 microns with a blade of nominal length. This compression rose to 28 microns for a blade length within specification limits but longer than nominal. A shorter than nominal blade length resulted in a compression of approximately 1.7 microns.

This is in contrast to a microkeratome cutting head assembly, in accordance with the present invention, such as that shown in FIG. 3. FIG. 3 shows apex 20 aligned with forward cutting edge 22 along line 46 which defines the apex 20 of trailing portion 18. As can be seen, a cornea 48 cut by the cutting head assembly of FIG. 3 does not compress the created corneal flap 50 and therefore, minimizes any chance of epithelial or other damage to the flap 50 that may have otherwise been caused by compression. The epithelial layer of cornea 48 can be said to be the darkest portion 52.

In testing with a computer model, with a cutting head assembly such as shown FIG. 3, using a cutting blade having a nominal length a compression of 0 microns was calculated. This is compared to the 10.9 microns of compression in the prior art. A more stark contrast can be found when blades of longer than nominal length are compared. Testing showed that such a longer blade resulted in compression of just 3.2 microns. This is compared to the 28 micron compression of a longer than nominal blade in the prior art. Therefore, not only does a nominal blade eliminate compression but a blade of longer than nominal length causes much less compression than is true of a longer blade in the prior art. This reduced sensitivity to variations in blade length also helps minimize the risk of epithelial damage during operation of microkeratome cutting head assembly 10. It is preferred, that the forward cutting edge 22 be placed within +/−5° relative to apex 20 to minimize compression of flap 50, as shown by lines 54. If edge 22 is placed beyond the preferred +/−5° from apex 20, the compression of flap 50 begins to be significant.

It will be appreciated that the predetermined distance defined by apex 20 and edge 22 determines the thickness of the flap created.

Not withstanding the preferred embodiments specifically illustrated and described above, it will be appreciated that various modifications and variations of the instance invention are possible in light of the description set forth above and the appended claims, without departing from the spirit and scope of the invention.

What is claimed is:

1. A microkeratome cutting head assembly comprising:
a cutting blade having a nominal length and presenting a forward cutting edge;
an applanation member for applanating a cornea of an eye and including a trailing portion having a curved section presenting an apex; and
wherein the forward cutting edge of the cutting blade of the nominal length is positioned relative to the apex, such that the forward cutting edge and the apex together define a desired thickness of a flap to be created from the cornea, such that the flap is essentially not compressed, thereby minimizing damage to the flap.

2. The assembly of claim 1 wherein the flap thickness is between 120 microns and 200 microns.

3. The assembly of claim 1 wherein the forward cutting edge is positioned within five degrees relative to the apex.

4. A microkeratome head assembly comprising:
a cutting blade having a nominal length and presenting a forward cutting edge; and
an applanation member for applanating a cornea of an eye and including a trailing portion having a curved section presenting an apex wherein the apex and the forward cutting edge cooperate to define a distance which creates a given corneal flap thickness to be formed from the eye, such that any compression of the corneal flap will be minimized during operation of the microkeratome head assembly.

5. The assembly of claim 4 wherein the distance between the apex and the forward cutting edge is between 120 microns and 200 microns.

6. The assembly of claim 4 wherein the forward cutting edge is positioned within five degrees relative to the apex.

* * * * *